United States Patent [19]

Brennan

[11] 4,270,548

[45] Jun. 2, 1981

[54] ALLERGY TESTING METHOD

[75] Inventor: Louis G. Brennan, Stockton, Calif.

[73] Assignee: Aller-Screen, Inc., Stockton, Calif.

[21] Appl. No.: 102,306

[22] Filed: Dec. 11, 1979

Related U.S. Application Data

[62] Division of Ser. No. 939,442, Sep. 5, 1979, Pat. No. 4,205,689.

[51] Int. Cl.³ .............................................. A61B 10/00
[52] U.S. Cl. ................................... 128/743; 128/253; 206/439
[58] Field of Search ................................. 128/743, 253

[56] References Cited

U.S. PATENT DOCUMENTS

| | | | |
|---|---|---|---|
| 2,522,309 | 9/1950 | Simon | 128/743 |
| 2,841,138 | 7/1958 | Laub | 128/743 |
| 3,034,507 | 5/1962 | McConnell et al. | 128/253 |
| 3,246,647 | 4/1966 | Taylor et al. | 128/253 |
| 3,289,670 | 12/1966 | Krug et al. | 128/743 |
| 3,291,129 | 12/1966 | Burelle et al. | 128/743 X |
| 3,556,080 | 1/1971 | Hein | 128/743 |
| 3,596,660 | 8/1971 | Melone | 128/253 |
| 3,688,764 | 9/1972 | Reed | 128/743 |
| 3,930,580 | 1/1976 | Bazell et al. | 206/439 |
| 4,091,922 | 5/1978 | Egler | 206/364 |

Primary Examiner—Kyle L. Howell
Attorney, Agent, or Firm—L. G. Wise

[57] ABSTRACT

A skin testing system for in vivo intracutaneous use which comprises a novel injection unit and multiple applicator means, each of the units carrying biological or chemical substances for skin testing, at least one of the units carrying a plurality of different antigens in admixture. Test substances are deposited intracutaneously by piercing the skin with each injection to predetermined depth; and the pierced skin is observed for response to the various substances and dermographia.

Each of the injection units includes a handle portion, hilt portion and a scarifier portion having means for carrying testing substances.

The preferred applicator means comprises points carrying groups of admixed allergens selected from tree allergens, mold allergens, grass allergens, ragweed allergens, weed allergens, dust, epidermals and foods together with histamine control, and diluent control.

16 Claims, 5 Drawing Figures

ALLERGY TESTING METHOD

This is a division of application Ser. No. 939,442, filed Sept. 5, 1979, now U.S. Pat. No. 4,205,689.

The present invention relates to skin testing with biological substances. In particular, it relates to medical methods and devices for allergy detection, including intracutaneous injection of biologicals, such as aeroallergens, food allergens, and other chemical substances.

Diagnosis of allergies in the past has depended upon a number of techniques for introducing various biological substances to the epidermis or dermis. In a widely-accepted testing method for inhalent allergy—the scratch test—various allergenic substances are applied by abrading or cutting the epidermal layer and contacting a liquid allergenic extract or the like with the exposed skin tissue. These test areas are often on the back of a human patient, who may be subject to many painful tests. This testing method is described in U.S. Pat. No. 2,841,133, which discloses a multiple unit device having a number of scarifiers in fluid communications with allergenic liquids.

The allergenic extracts may be applied manually or by automatic means. Another device for simultaneously producing multiple cutaneous sites by abrading the skin and applying biologicals is described in U.S. Pat. No. 3,289,670. The superficial scratches or abrasions produce a less severe reaction than dermal injection. If no response or weak responses are obtained in the scratch tests, less concentrated allergens may be applied to the upper extremities of the patient intradermally with a small bore needle and syringe. Reactions to these latter tests may be dramatic and even require emergency measures due to the severity of the reaction.

In another allergy testing method, a series of intradermal injections is administered by the laborious needle and syringe procedure, employing allergens in various dilutions for safety and therapeutic reasons. This serial dilution technique requires a highly skilled technicial and is tedious, expensive, and often painful to the patient. However, these in vivo allergy testing methods are the primary test methods employed by allergists and otolaryngologists currently. In vitro test methods, such as radioimmunoassays, require considerable laboratory equipment and are not generally accepted for screening patients on a preliminary basis.

In addition to the airborne allergens, food allergens have been tested by skin response and are of interest to many workers in the medical field.

Besides the epidermal scratch and intradermal allergy testing methods, scarifiers have found use in applying other biological substances. For instance, vaccinations may be effected with such devices, as taught in U.S. Pat. Nos. 3,291,129 and 3,596,660. Antigens have been applied intradermally for the Heaf multiple puncture tuberculin test, as disclosed in U.S. Pat. Nos. 3,034,507 and 3,688,764.

Various attempts have been made to simplify the testing of allergies to reduce the amount of time necessary for effecting application of allergenic substances. In U.S. Pat. No. 3,556,080, multiple skin tests are administered simultaneously by applying a plurality of spaced scarifiers or puncture heads dipped in liquid antigens; however, this method has not proven entirely satifactory due to the difficulty of locating a number of effective test sites in predetermined geometric pattern. Care must be taken in administering intradermal antigens not to inject the biological substance into a blood vessel, and this limitation on the practical use of spaced multipoint applicators has discouraged its adoption for intradermal testing.

The present invention provides a system for allergy testing wherein common antigens are incorporated in a plurality of injector units adapted for intracutaneous use. The individual injector units are intended to be supplied as part of a multiple-allergen screening and/or diagnostic kit.

A new skin test device for intracutaneous or intradermal use has been devised. This device is an applicator or injection unit having a hilt or flat plate portion and a hollow rigid handle portion attached to the plate portion on one side thereof and adapted for grasping the device. In order to pierce the skin, a hollow metal cannula scarifier element is mounted on the flat plate, extending outwardly from the flat plate opposite the handle portion a predetermined length for intradermal injection. The cannula has a sharp skin-piercing point at its lower extremity and a shaft portion extending upwardly through the flat plate into said hollow handle portion. This configuration permits the device to be loaded with a predetermined amount of fluent skin testing substance, which may be applied to the point by dipping and distributed into the hollow scarifier by capillary action.

The flat plate portion and handle portion may be integrally molded of thermoplastic resin, such as polypropylene. In the preferred embodiment of the skin test device, the handle portion comprises an elongated cylindrical tube having an open top end, and the flat plate portion has a sleeve projecting upwardly into the hollow handle portion for holding the scarifier element firmly with a predetermined prong length exposed below the hilt.

An allergy testing kit for multiple allergen screening may be assembled with a number of these applicators or injection units. A base member comprising a plurality of recessed depressions, each having a well portion adapted to receive a needle-like prong, is provided with the kit. A corresponding number of intracutaneous injection units adapted for being held in the recessed depression of the base member is provided, each comprising a hilt portion adapted for insertion into a complementary recessed depression of the base member. A downwardly extending skin test prong portion is adapted for insertion into the corresponding well. The upwardly extending handle portion can be grasped manually for applying the injection units sequentially. In the test kit at least one of the prongs is loaded with a mixture of biologically active allergens, at least one of the prongs is loaded with a histamine control substance, and at least one of the prongs is loaded with a diluent devoid of biologically active substance.

The assembled kit may include a sealed package of ethylene-oxide-permeable material for containing the base member and injection units, permitting sterilization after assembly. Advantageously, the test prongs comprise a hollow cannula or hypodermic needle extending from the hilt into the base well about 0.5 to 3 mm, and the handle portion is hollow to receive an upper shaft portion of the cannula. This permits capillary loading of the prongs by dipping the prong into a liquid.

The invention will be further explained in the following description and in the drawing, wherein.

In the following description, all measurements and dimensions are given in metric units and parts by weight unless otherwise stated.

Figure 1:
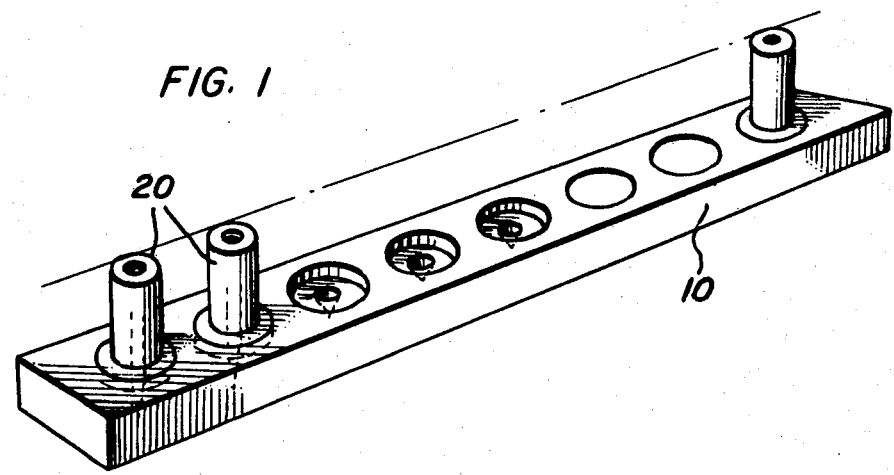
FIG. 1 is a perspective view of the novel applicator system, showing the base and an injection unit.
Figure 2:
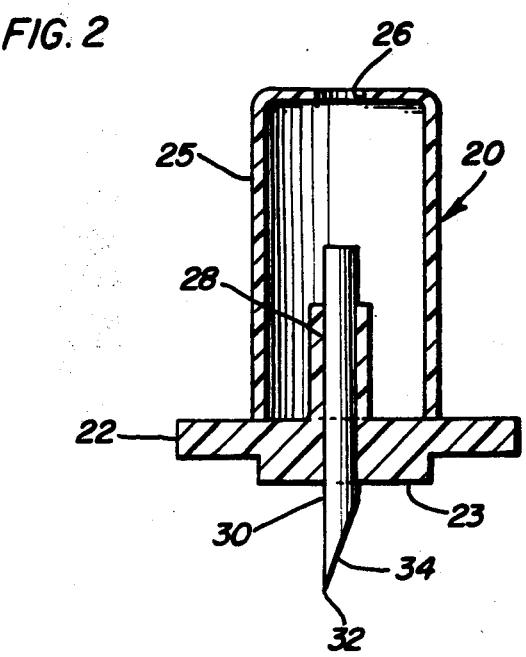
FIG. 2 is a vertical cross-section view of an injection unit.

Referring to FIG. 1 a base member 10 in the form of a stable flat tray is provided with a plurality of recessed depressions 12 adapted to receive individually removable applicators or injection units 20. The depressions are aligned in one or more rows for ease of identification and to facilitate use of the individual applicators. An enlarged sectional view of a single injection unit 20 is depicted in FIG. 2. In this preferred embodiment, a metal cannula is held firmly in the hilt portion 22 of the injection unit. The hilt portion comprises a flat plate, with a two-tier configuration 22,23. The handle portion 25, shown as an elongated cylindrical tube, may have an opening at its top end or elsewhere to permit gas access to the interior of the injection unit. This aids in manufacture, liquid loading and sterilization of the fabricated applicator system. To provide a firm gripping force on the cannula 30, the flat plate or hilt portion 22 of the injection unit has a sleeve 28 projecting upwardly into the hollow handle portion. This prevents slippage during use of the cannula 30 as a scarifier, with a predetermined length exposed below the flat plate or hilt 22, 23.

During loading of liquid biologicals or other fluid materials, the cannula may be dipped into the fluid, with the skin-piercing point 32 being received into a well to prevent damaging the point. A hollow portion 34 provides a liquid reservoir on the cannula scarifier element 30, 32.

Figure 3:
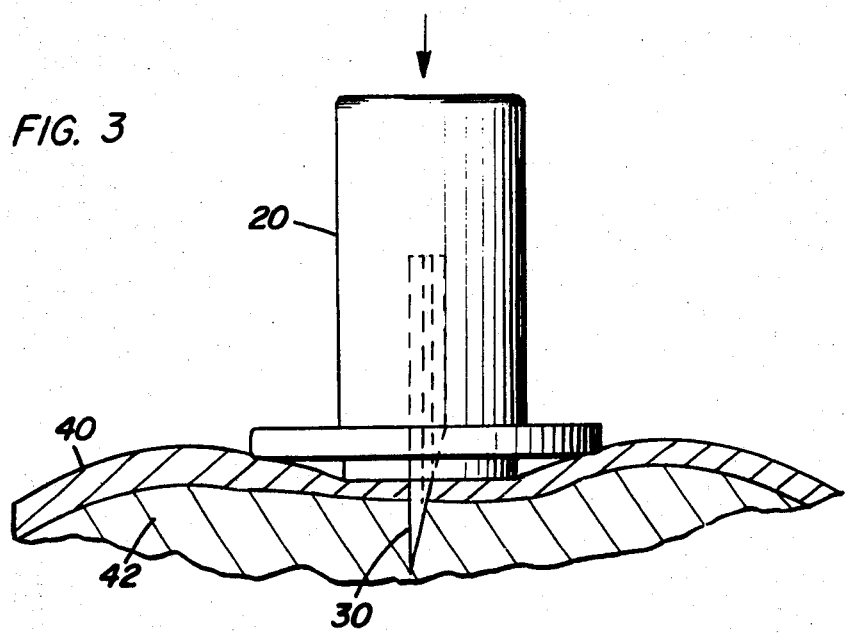
FIG. 3 is a schematic view of the injection unit during use.
Figure 4:
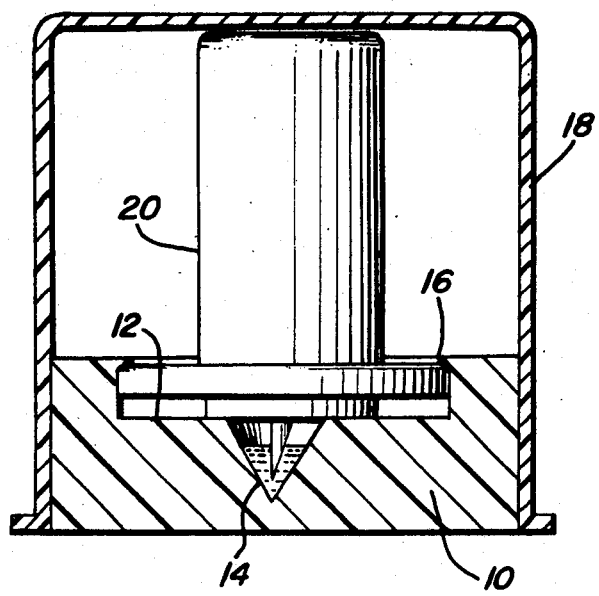
FIG. 4 is a vertical cross-section view of the package base containing an injection unit.

During use for skin testing, the injection unit 20 is removed manually from the base and inserted into the skin, as shown in FIG. 3. The hollow metal scarifier element 30 pierces the epidermal layer 40 and extends therethrough into the dermis 42, where the substance carried on the scarifier prong is deposited intracutaneously. Ordinary, the injection unit is withdrawn immediately after injecting the test substance. The base member 10 may be packaged as part of a testing kit, as shown in FIG. 4. The base is provided with a plurality of circular depressions 12 into which the hilt portion of injection unit 20 is inserted. The bottom of this recessed portion is tapered downwardly to a depth of about 3 mm, permitting the lower prong tip 32 to be accommodated within a well 14, which may be conoidal in shape. Prior to inserting the injection unit. a measured quantity of the particular biological substance or diluent is placed in the bottom of the well 14. In order to protect the testing kit after manufacture and sterilization, a lid 18 is placed over the base member 10, preventing the individual injection units from becoming loose. As an extra precaution, a projecting segment 16 can be molded onto the base 10 to engage or retain the hilt portion in its nested position, thus preventing dislocation of the applicator parts during shipment. The lid may be taper-fitted with the sides of base member 10 to prevent contamination of the applicator and/or antigens. The lid and base may be spot-fused to prevent disassembly prior to use. The enclosure formed by the base and lid may be pre-sterilized or, advantageously, made of a material permeable to a sterilant gas. For instance, various polyalkenes, such as polyethylene, may be employed as the package material when using ethylene oxide/freon gas for post-assembly sterilization. Alternatively, the entire testing kit may be inserted in an envelope having a gas-permeable window.

The applicator prong or skin-piercing portion of the injection unit may be made from several materials, preferably metal and hard plastics. Polished surgical steel cannulae are the prong members found to be advantageous from the standpoint of quality and reproducibility. The standard hypodermic needle or cannula of polished steel, having a bevel angle of 12.5°, provides a sharp point which can easily be inserted to the desired skin depth. A standard cannula of 15 to 25 gauge can be employed, depending upon the desired carrying capacity of the base structure and prong size. For a wide variety of biological substances, a standard 20 gauge cannula can provide the dual functions of the prong member. The diluent or fluid carrier of the biologicals is often a hydrophilic compound or mixrture of chemicals which possesses a high surface tension with respect to the prong. A capillary-forming structure permits relatively large amounts of the liquid biological substances and carriers to adhere to the prong. Typically, a 20 gauge steel needle has been found to retain about 1.8 milligrams of antigen-diluent mixture after dipping.

While the amount of fluid varies according to the particular test composition and prong type, amounts from a few tenths of a millimeter to a few microliters may be feasible. For allergenic extracts of the kinds described herein, a loading of about 0.001 to 0.1 ml is preferred. Liquid pickup from the polypropylene type base would ordinarily be in the desired range if a fractional milliliter of liquid extract or chemical mixture is contained in the well. It is understood that a controlled amount of solid or semi-dried biological can be obtained by employing more or less diluent to adjust the active component of the mixture. A relatively large amount of antigen can be picked up by surface phenomena when less diluent is present. For purposes of product uniformity, the amounts of antigen components can be as set forth herein or some other standard may be established for manufacturing convenience or medical purpose.

Plastic molding compositions, such as nylons, polyalkenes, polycarbonates, acrylics, etc. can be employed in making the injection units, bases, covers, etc. Provided an effected point can be cast or molded from plastics, the entire system may be fabricated from one or more synthetic resins. In the preferred embodiments, metal prongs and thermoplastic resin, such as polypropylene, are used.

The flat base of the applicator may be two-tiered with a central smaller portion adjacent the cannula and a larger portion near the handle. This type of base disguises the needle puncture and serves as a stop to control depth of penetration of the point of the test prong.

This feature makes the needle puncture virtually painless and insures repetitive, standardized penetration of the skin to the desired depth. An alternative design is a completely flat hilt.

Aside from the obvious advantage of the hypodermic needle point; i.e., sharp, relatively atraumatic skin puncture, there are other advantages. These advantages are the utilization of the inner bore of the needle, in the area of the cutting point or bevel, as an inherent capillary trough or liquid reservoir for antigen application.

The needle point may project from the circular base anywhere from 0.5 to 3.0 mm or more, with 2.25 mm being optimum for most applicators. The injection unit permits the length of needle point projection to be varied without changing the cavity mold used in manufacture.

The preferred injection unit of FIG. 2 is made of a molded polypropylene plastic. The cylindrical handle is hollow with a wall about 1.6 mm thick. The elongated tubular shape (about 17.5×9.5 mm diameter) permits easy grasping. The two-tier circular hilt is about 2 mm thick at the inner circle (8.25 mm) and about 1.5 mm thick for the outer (15.25 mm). The cannula point and shaft pierce the center of the base, which is molded with a diameter slightly less than the cannula to provide means for holding the cannula in a fixed position by radial gripping force. The cannula shaft is additionally supported by a sleeve or cylindrical upward extension of the base for a distance of about 6 mm into the hollow core handle. The top of the handle is open to allow insertion of the cannula therethrough and to retain the capillary action.

Figure 5:
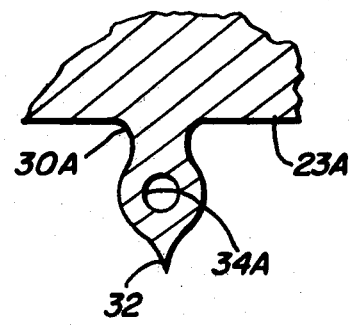
FIG. 5 is a partial cross-section view of an alternative embodiment.

An all-plastic alternative embodiment is shown in FIG. 5, an enlarged cross-sectional view showing the flat plate or hilt portion 23A having a hard prong portion 30A extending downwardly therefrom. The prong comprises a skin-piercing point 32A and a reservoir-forming open portion 34A, which is shown as an eyelet having an open area to receive liquid and hold it prior to application. The prong portion may have an overall length of 2-4 mm. If sufficient liquid holding capacity is achieved by the prong configuration, the eyelet may be omitted.

While the preferred testing method employing the new applicators involves a manual sequence in which the individual injections are spaced, at least about 2 cm apart on the skin, it is understood that the invention may be adapted or modified to permit simultaneous pickup and application of the entire multi-unit assembly. This can be accomplished by a suitable manipulator device adapted to receive and hold the handle portion of the individual injection units in spaced relationship. However, the aforementioned difficulties in avoiding blood vessels must be taken into account for any such multi-point application.

The number of wells for the base, and their geometric arrangement, can be adapted for several types of test kits. Ordinarily, about 8 to 11 unit will be required to provide optimum allergy screening capacity. If the injection device is employed for other biologicals, such as immunogens, a different base arrangement may be adapted.

The preferred allergy screening and/or diagnostic method for using the applicator kit includes placing common antigens into groups of closely related components for simplicity of testing. Typically, inhalent or aeroallergens are divided into seven or eight groups depending on the antigens found in a particular geographical location. Food antigens may also be divided into groupings.

These antigens are then applied by the individual injection units to the volar surface of the forearm along with controls of the particular diluent used and one of histamine. The purpose of using a control consisting essentially of the diluent (devoid of biologically active matter) is to insure against false positive reactions caused by sensitivity to the diluent itself or dermographia. The purpose of using a histamine control is to guard against false negative responses brought about by the patient having taken or having had admininstered a drug having antihistaminic properties within the previous twenty-four to forty-eight hour period (diminished host response).

The preferred groupings of inhalant antigens include the following North American biologicals: trees, molds, grasses, ragweed (Midwest and East coast), weeds, Bermuda, dust, and epidermals (dander, animal hair, feathers, etc.).

Different and new groupings may be employed, as local conditions determine, and geographical breakdown of the United States into nine territories for the purpose of antigen grouping has been established. Common antigens to all of these areas (and Canada) consist of grasses, weeds, molds, epidermals and house dust. Consequently, allergy testing kits supplied to all North American areas and elsewhere may have these common antigens plus the diluent and histamine controls. Kits supplied to the eastern and midwestern U.S. location Zones I through VI should have a separate applicator with short and giant ragweed. The most variable antigen tested for is that of the trees. Each geographical location should be individualized accordingly:

Zone I—New England States: Trees tested for will be as follows: Poplar, Maple, Box Elder, Elm and Oak.
Zone II—Eastern Seaboard: Poplar, Maple, Box Elder and Oak.
Zone III—Southeastern States: Poplar, Cottonwood, Oak, Pecan and Hickory.
Zone IV—Southcentral States: Poplar, Cottonwood, Elm, Cedar and Juniper.
Zone V—Midwest States: Poplar, Cottonwood, Oak, Ash and Walnut.
Zone VI—Northern Mid States: Poplar, Cottonwood, Maple and Box Elder.
Zone VII—Midwestern States: Maple, Box Elder and Sycamore.
Zone VIII—Farwest Northern States: Poplar, Cottonwood, Oak and Evergreens.
Zone IX—Far Southwestern Coast: Poplar, Box Elder, Oak, Walnut, Olive, Sycamore, Chinese Elm, Hackberry, Mulberry, Ash and Cottonwood.

Because of the large number of trees to be tested in the Southwestern states, there should be two applicators per kit. One will be the major pollinating trees and the other the minor pollinating trees.

Canada has the common antigens previously mentioned. Tree antigens have been broken down into provinces. These are as follows:
British Columbia: Same as Zone VI and VII
Alberta: Same as Zone VI
Saskatchewan: Same as Zone VI
Manitoba: Same as Zone I, V and VI
Ontario: Same as Zone I
Quebec: Same as Zone I Food antigens have been classified into common families numbering nine. They are the following:
I. Whole Cow's Milk
II. Whole Egg
III. Legumes (peas, peanuts and all beans including soybean)
IV. Chocolate
V. Grains (wheat, rye, barley and corn)
VI. Citrus fruits (orange, grapefruit and lemon)
VII. Potato family (including green pepper, tomato and potato)

VIII. Seafood and fish family

IX. Cucumber family (cucumber, cantaloupe and watermelon)

The antigen may be applied to the applicator tip in either an aqueous form or a glycerin-saline base. The aqueous form consists of methyl paraben 0.5% and propylparaben 0.05% in N. saline solution. The aqueous antigen can be concentrated on the applicator prong by packaging the units with silica gel or other dessicant.

The antigen may be dehydrated by controlled temperature dehydration; i.e., less than 39° C., to prevent denaturing the biologicals. This dehydrated form of antigen has adequate shelf-life and becomes biologically active when introduced into the skin. The glycerin-saline base antigen (equal volumes of glycerin and N. saline) is simply applied to the tip of the applicator by dipping and left in a nondehydrated state for shipment and use.

Antigens may be applied in mass production by filling the corresponding well of the base, in which the applicator is housed for shipment. The advantage of this method is less labor and expense of production as well as adequate stability and shelf-life.

Since the cannula is electrically conductive, certain biological substances can be deposited electrophoretically from a suitable aqueous or nonaqueous dispersion by biasing the cannula with a direct current potential.

For trees, weeds, and grasses, the preferred concentration is 50 grams/liter (g/l). For mold, epidermals and house dust, the preferred concentration is 100 g/l. These concentrations will render 20,000 protein nitrogen units per c.c. Because of the 50% glycerin, the shelf-life of the antigen is several years. Individual kits are assembled and gas sterilized with a gaseous mixture of 88% ethylene oxide and 12% Freon. Preferably each kit will have two controls, one control consisting of histamine phosphate (0.55 g/l). The other control of a blank control consisting of glycerin and saline.

It is advantageous to provide distinctive markings on each injection unit. The different antigen groups and controls may have a different colored applicator for coding. The base may have recessed depressions of particular individual shape to accommodate a distinctive hilt shape for each biological or control substance. For instance, the flat plate may be in a circular, oval, square, triangular, octagonal or other desired shape to prevent confusion.

This invention is a new diagnostic and diagnostic screening technique for use in inhalent allergy (aeroallergens) and food allergy. It incorporates the use of a unique antigen applicator. Any physician or supervised staff can, by use of the test kit, diagnose and/or screen a patient for inhalent or food allergy. This is accomplished simply, inexpensively, accurately and virtually painlessly. In addition, this technique is inherently safer than many current intradermal allergy testing methods.

If a patient or subject does not give positive reactions to the initial testing, there is probably no significant aeroallergen or food sensitivity. This obviates the need of subjecting the patient to needless, costly and time-consuming further testing. If on the other hand, the patient demonstrates a positive reaction to multiple-allergen testing, further delineation of the offending antigen can then be conducted via either scratch testing, specific intradermal or the serial dilution technique. The practitioner may treat the patient in a known manner by injecting the multiple-antigen mixture to which a positive reaction has been observed. Likewise, an individual component of a positive antigem mixture may be employed for hyposensitization after identification of the antigen by delineating the mixture. In addition to the benefits of reduced cost in time and money, as well as discomfort from numerous allergy tests, the chances of untoward reaction are reduced numerically by use of the present system.

While the invention has been described by particular example, there is no intent to limit the inventive concept except as set forth in the following claims.

What is claimed is:

1. A skin testing method for in vivo intracutaneous use which comprises the steps of:

providing applicator means comprising a plurality of individual injection units, each of said injection units comprising a handle portion, a hilt portion and a scarifier portion comprising a skin piercing intradermal point and having means for carrying testing substances, each of said units carrying biological or chemical substances for skin testing, at least one injection unit of said applicator means carrying a plurality of different antigens in admixture;

depositing said substances intracutaneously by piercing the skin with each unit to predetermined depth; and observing the pierced skin for response to said substances and dermographia.

2. The method of claim 1 wherein the applicator means comprises at least one injection unit loaded with a predetermined effective amount of admixed allergens selected from tree allergens, mold allergens, grass allergens, ragweed allergens, dust, epidermals and weed allegens; and wherein said applicator means further comprises histamine control substance and diluent control substance.

3. The testing method of claim 1 wherein said antigen is provided in a concentration of about 50 to 100 grams per liter.

4. The testing method of claim 1 wherein said hilt portion comprises a two-tier configuration with a small central tier portion adjacent said scarifier portion and a large tier portion adjacent said handle portion.

5. The testing method of claim 1 wherein at least one of said biological substances comprises a mixture of aero-allergens.

6. A skin test method for in vivo intracutaneous use which comprises: loading a liquid biological test substance onto a skin-piercing prong element of at least one applicator unit comprising a plate portion; a holow rigid handle portion attached to the plate portion on one side thereof and adapter for manually grasping the device; and a hollow cannula prong element mounted on said plate and extending outwardly from said plate opposite said handle portion a predetermined length for intracutaneous injection, said cannula having a sharp skin-piercing point at its lower extremity and an upper shaft portion extending upwardly through said plate into said hollow handle portion, whereby said applicator unit may be loaded with a predetermined amount of skin testing substance applied to said point by dipping and distributed into the cannula by capillary action; and applying said applicator unit to a skin test area, thereby depositing a predetermined amount of test substance.

7. The skin test method of claim 6 comprising at least one applicator unit load with an effective amount of admixed allergens selected from tree allergens, mold allergens, grass allergens, ragweed allergens, epidermals, dust and weed allergens; and further comprising applicator units loaded separately with histamine control substance and diluent control substance.

8. The skin test method of claim 7 wherein said allergen is provided in a total concentration of about 50 to 100 grams per liter.

9. The skin test method of claim 6 wherein said plate portion includes a two-tier configuration having a small central hilt portion adjacent said cannula and larger outer plate portion recessed from said inner hilt portion, thereby disguising puncture of said cannula point and providing standardized skin penetration.

10. An allergy testing procedure for multiple allergen screening comprising: loading a plurality of intracutaneous injection units with different liquid test substances, each of said injection units comprising a hilt portion, an upwardly extending handle portion and a downwardly extending skin test prong portion having reservoir means for holding a predetermined quantity of said liquid test substances; at least one of said prongs being loaded with a mixture of biologically active allergens; at least one of said prongs being loaded with a histamine control substance; and at least one of said prongs being loaded with a diluent devoid of biologically active substance; applying said injection units to a plurality of spaced apart skin test areas thereby depositing a predetermined effective and safe amount of liquid test substances; permitting allergic reaction to develop; and observing the skin test areas for allergic reaction.

11. An allergy testing procedure according to claim 10 wherein said biologically active allergens are applied in groups of admixed allergens comprising at least one tree aero-allergen extract group, at least one mold aero-allergen group, at least one grass aero-allergen group, at least one weed aero-allergen group and at least one epidermal aero-allergen group; each of the individual aero-allergens being provided in predetermined effective amount.

12. The allergy testing procedure of claim 10 wherein said liquid test substance comprises at least one mixture of multiple food antigens.

13. A skin testing method comprising the steps of:

providing a base member comprising a plurality of recessed depressions, each having a well portion adapted to receive a needle-like prong;

providing a plurality of intracutaneous injection units held in the recessed depressions of said base member and individually removable therefrom, each of said injection units comprising a hilt portion adapted for insertion into the recessed depression of said base member, an upwardly extending handle portion and a downwardly extending skin test prong portion adapted for insertion into a corresponding well wherein each prong comprises a hollow metal cannula extending from the hilt into the corresponding well, and wherein the handle portion of each injection unit is hollow to receive an upper portion of said cannula, thereby permitting capillary loading of the prongs by dipping the prong into a liquid;

loading at least one of said prongs with biologically active allergen; loading at least one of said prongs a histamine control substance; loading at least one of said prongs a diluent devoid of biologically active substance;

depositing the allergen, histamine control and diluent substances intracutaneously by inserting the hollow metal cannula of each unit into a skin area to be tested; and permitting an allergic reaction to develop in the skin test area.

14. The method of claim 13 wherein each hollow metal cannula extends from the hilt about 0.5 to 3 mm. and wherein the handle portion of each injection unit is hollow to receive an upper portion of said cannula, thereby permitting capillary loading of the prongs by dipping the prong into a liquid.

15. The method of claim 14 wherein the hollow cannula has a reservoir capacity for loading about 0.001 to 0.1 ml of liquid.

16. The method of claim 15 wherein said injection unit comprises a 20 gauge cannula having a liquid capacity of about 1.8 milligrams and an exposed length of about 2.25 mm.

* * * * *

UNITED STATES PATENT AND TRADEMARK OFFICE
CERTIFICATE OF CORRECTION

PATENT NO. : 4,270,548

DATED : 2 June 1981

INVENTOR(S) : LOUIS G. BRENNAN

It is certified that error appears in the above—identified patent and that said Letters Patent is hereby corrected as shown below:

Column 4, line 22; change "mixrture" to -- mixture --.

Column 5, line 48; change "unit" to -- units --.

Column 8, line 1 ; change "antigem" to -- antigen --.

Column 8, line 50; change "holow" to -- hollow --.

Signed and Sealed this

Sixteenth Day of March 1982

[SEAL]

Attest:

Attesting Officer

GERALD J. MOSSINGHOFF

Commissioner of Patents and Trademarks